(12) United States Patent
King

(10) Patent No.: US 10,041,251 B2
(45) Date of Patent: Aug. 7, 2018

(54) FLOOR JOIST

(71) Applicant: Mid-Columbia Lumber, Bend, OR (US)

(72) Inventor: Randy King, Bend, OR (US)

(73) Assignee: Mid-Columbia Lumber, Bend, OR (US)

( * ) Notice: Subject to any disclaimer, the term of this patent is extended or adjusted under 35 U.S.C. 154(b) by 0 days.

(21) Appl. No.: 15/351,081

(22) Filed: Nov. 14, 2016

(65) Prior Publication Data

US 2017/0138049 A1 May 18, 2017

Related U.S. Application Data

(60) Provisional application No. 62/254,820, filed on Nov. 13, 2015.

(51) Int. Cl.
| | |
|---|---|
| *E04C 3/12* | (2006.01) |
| *E04C 3/14* | (2006.01) |
| *B07C 5/14* | (2006.01) |
| *G01D 5/26* | (2006.01) |
| *G01N 3/32* | (2006.01) |
| *F16B 11/00* | (2006.01) |

(52) U.S. Cl.
CPC ................ *E04C 3/12* (2013.01); *B07C 5/14* (2013.01); *E04C 3/14* (2013.01); *F16B 11/006* (2013.01); *G01D 5/268* (2013.01); *G01N 3/32* (2013.01); *G01N 2203/0296* (2013.01); *Y10T 403/7045* (2015.01)

(58) Field of Classification Search
CPC ......... Y10T 403/7045; Y10T 156/1075; Y10T 428/192; B27F 1/16; E04C 3/02; E04C 3/12; E04C 3/14; E04C 3/122; F16B 11/006; F16B 2012/043; F16B 2012/046; F16B 5/0012; B07C 5/14; G01D 5/268; G01N 3/32; G01N 2203/0296

See application file for complete search history.

(56) References Cited

U.S. PATENT DOCUMENTS

| | | | | |
|---|---|---|---|---|
| 3,480,054 A | * | 11/1969 | Marian ..................... | B27F 1/16 144/347 |
| 4,074,498 A | * | 2/1978 | Keller ....................... | E04C 3/14 52/690 |
| 4,624,295 A | * | 11/1986 | Howland ................... | B27F 1/00 144/347 |
| 4,907,383 A | * | 3/1990 | Winter, IV ............... | E04C 2/296 52/309.9 |

(Continued)

*Primary Examiner* — Joshua J Michener
*Assistant Examiner* — Matthew J Gitlin
(74) *Attorney, Agent, or Firm* — Leydig, Voit & Mayer, Ltd.

(57) ABSTRACT

A floor joist including a first piece of lumber including a first set of fingers and a first set of grooves is provided. A second piece of lumber including a second set of fingers and a second set of grooves is also provided. A finger joint is formed by a combination of the first second of fingers with the second set of grooves and a combination of the second set of fingers with the first set of grooves. A first set of pockets are formed between the combination of the first second of fingers with the second set of grooves, and a second set of pockets are formed between the combination of the second set of fingers with the first set of grooves.

6 Claims, 2 Drawing Sheets

(56) References Cited

U.S. PATENT DOCUMENTS

Figure 1:
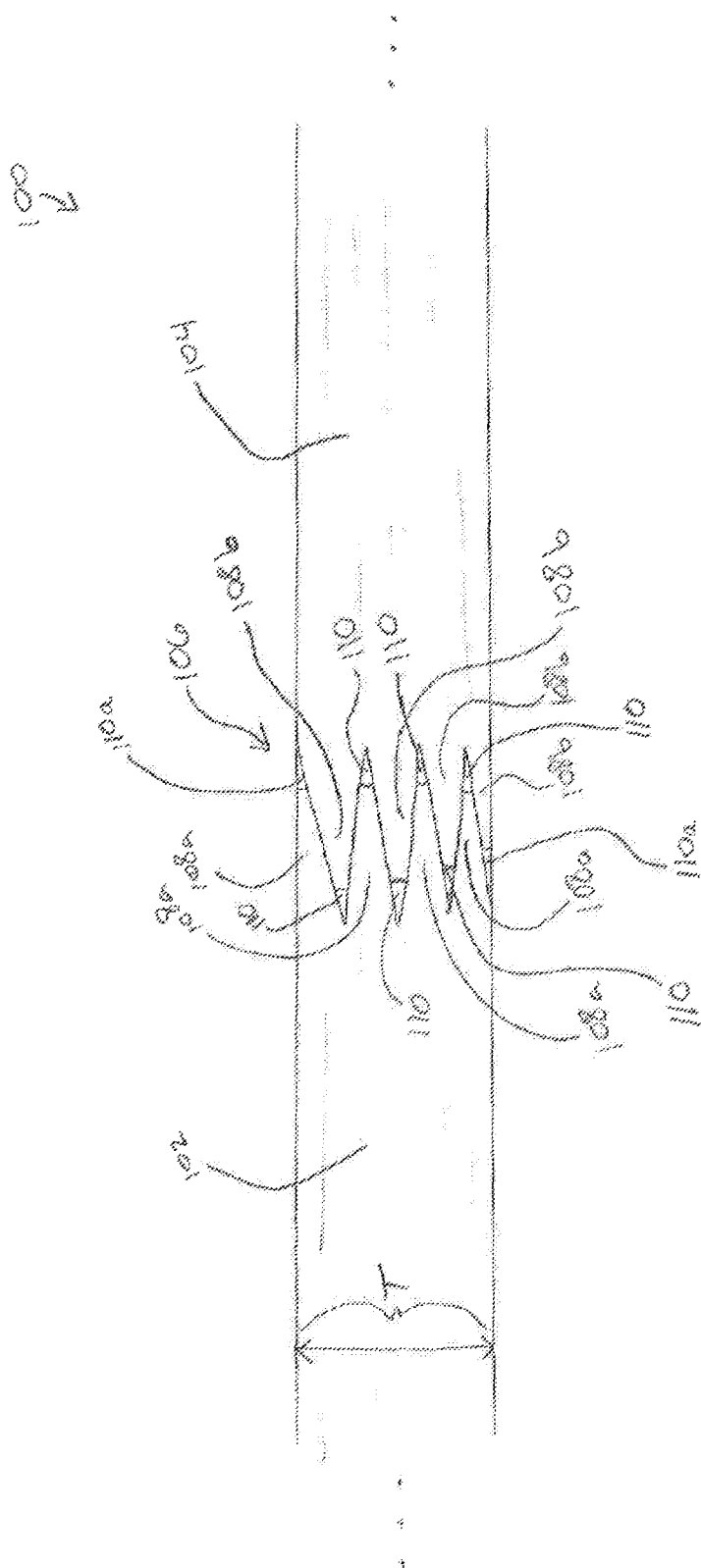

| | | | | |
|---|---|---|---|---|
| 5,114,265 A * | 5/1992 | Grisley | B27F 1/12 | 144/144.1 |
| 5,165,816 A * | 11/1992 | Parasin | E04C 2/10 | 403/334 |
| 5,960,104 A * | 9/1999 | Conners | G01N 21/8986 | 144/402 |
| 6,023,900 A * | 2/2000 | Stoehr | B27M 3/002 | 403/364 |
| 6,025,053 A * | 2/2000 | Grenier | B07C 5/14 | 144/332 |
| 6,068,034 A * | 5/2000 | Phelps | B23D 59/008 | 144/3.1 |
| 6,358,352 B1 * | 3/2002 | Schmidt | B07C 5/14 | 144/344 |
| 6,378,579 B1 * | 4/2002 | Giltner | B27F 1/16 | 144/345 |
| 6,450,235 B1 * | 9/2002 | Lee | B27L 5/00 | 160/236 |
| 6,701,984 B2 * | 3/2004 | Lamontagne | B27M 1/08 | 144/3.1 |
| 6,860,071 B2 * | 3/2005 | Weaber | B27M 3/04 | 428/172 |
| 7,068,050 B2 * | 6/2006 | Steele | G01N 22/04 | 324/640 |
| 8,261,508 B2 * | 9/2012 | Thiers | E04F 15/02 | 428/192 |
| 8,424,577 B2 * | 4/2013 | Poutanen | B27F 1/16 | 144/347 |
| 8,652,292 B2 * | 2/2014 | Baillargeon | B27H 1/00 | 144/381 |
| 2002/0034416 A1 * | 3/2002 | Lichtenberg | B27D 1/10 | 403/270 |
| 2002/0076275 A1 * | 6/2002 | Hernandez | B27D 1/10 | 403/364 |
| 2007/0220825 A1 * | 9/2007 | Davis | B27G 1/00 | 52/847 |
| 2007/0234860 A1 * | 10/2007 | Stanish | B27B 1/007 | 83/14 |
| 2008/0099105 A1 * | 5/2008 | Kelly | B27M 1/08 | 144/371 |
| 2008/0236704 A1 * | 10/2008 | Risi | B23D 59/001 | 144/356 |
| 2015/0114519 A1 * | 4/2015 | Hyde | A01G 3/08 | 144/4.1 |

* cited by examiner

FLOOR JOIST

CROSS-REFERENCE TO RELATED APPLICATIONS

This patent application claims the benefit of U.S. Provisional Patent Application No. 62/254,820, filed Nov. 13, 2015, which is incorporated by reference.

BACKGROUND OF THE DISCLOSURE

A joist is typically a load bearing member that is configured to provide structural support in a building. For instance, a floor joist is typically a horizontal member that spans a distance between two walls and supports a floor of a building and any objects on the floor of the building. Depending on the dimensions of the floor the floor joist is designed to support, the floor joist may include multiple connected pieces of material to achieve a desired length. For instance, for a floor joist made from wood, the floor joist may include multiple pieces of lumber connected together at one or more joints of the floor joist.

Generally, building construction is regulated by a variety of building codes, as typically provided by the International Residence Code (IRC) for residential construction and the International Building Code (IBC) for non-residential construction. Typically, building codes provide parameters to which various portions of the building must adhere. For instance, a floor joist must be designed to carry a specified amount of weight for various types of buildings. Further, a floor joist constructed from wood must meet some regulations regarding the fire resistance of the floor joist.

BRIEF SUMMARY OF THE DISCLOSURE

One embodiment provides a floor joist including: a first piece of lumber including a first set of fingers and a first set of grooves; a second piece of lumber including a second set of fingers and a second set of grooves; and a finger joint formed by a combination of the first set of fingers with the second set of grooves and a combination of the second set of fingers with the first set of grooves. A first set of pockets are formed between the combination of the first second of fingers with the second set of grooves, and a second set of pockets are formed between the combination of the second set of fingers with the first set of grooves.

Another embodiment provides a method of manufacturing a floor joist. The method includes: performing an optical inspection of a package of lumber; separating the package of lumber into three groups of lumber based on engineering grade; performing a mechanical inspection of each of the three groups of lumber; sorting each piece of lumber of the three groups of lumber into more than three groups of lumber based on a refined engineering value determined based on the mechanical inspection; and manufacturing the floor joist using lumber entirely from one of the more than three groups of lumber based on a desired engineering value for the floor joist.

BRIEF DESCRIPTION OF THE DRAWING(S)

Figure 2:
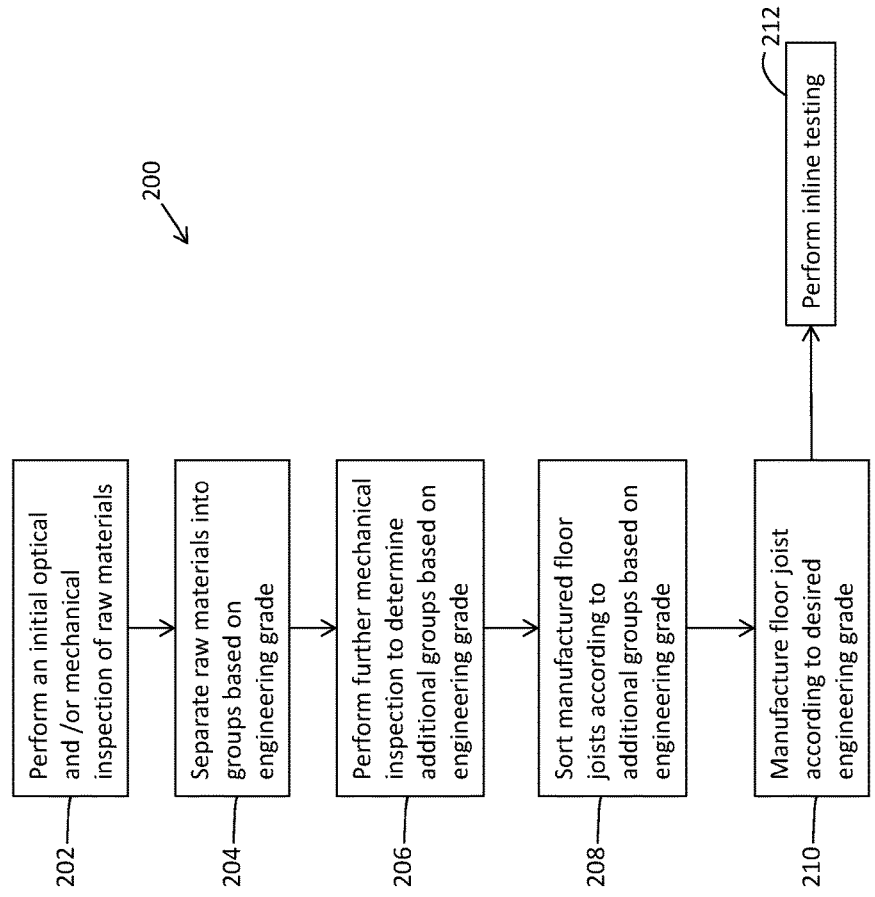

The accompanying drawings incorporated in and forming a part of the specification illustrate several aspects of the present disclosure and, together with the description, serve to explain the principles of the disclosure. In the drawings:

FIG. 1 is a cross-sectional view of a joint of a floor joist, in accordance with an embodiment of the disclosure; and FIG. 2 is a method of manufacturing the floor joist of FIG. 1.

While the disclosure will be described in connection with certain embodiments, there is no intent to limit it to those embodiments. On the contrary, the intent is to cover all alternatives, modifications and equivalents as included within the spirit and scope of the disclosure as defined by the appended claims.

DETAILED DESCRIPTION OF THE DISCLOSURE

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Various embodiments of the present disclosure provide a floor joist that is constructed with wood with exceptional strength, as graded under that standards set by the Western Wood Products Association (WWPA). These floor joists may be used in either vertical or horizontal applications. In certain embodiments, the floor joist will have a thickness of approximately two inches, a width of either approximately ten inches or twelve inches and a length between approximately eight feet and approximately sixty feet. Other dimensions are contemplated, and as such, the specified dimensions are just illustrative of certain embodiments.

FIG. 2 illustrates a method 200 of manufacturing a floor joist in accordance with an embodiment of the disclosure. At step 202, a visual or optical and mechanical inspection of raw materials of the floor joist is performed prior to constructing the floor joist. A process of the optical and mechanical inspection begins with purchasing the raw materials, which comes in a three grade package from a certified lumber provider. The grade spectrum includes three types of wood graded as a number 1, a number 2 or as what is called select structural. These grade levels are specified by the WWPA. The number 2 grade is typically the lowest grade and generally includes wood with a modulus of elasticity or E grade or, in other words, an engineering value approximately around 1.6e. The number 1 grade is a middle level grade and includes wood with an engineering value approximately around 1.8e. And the select structural grade is the highest grade with an engineering value approximately around 1.9e. Generally, in a package from the certified lumber provider, 15% of the package will be of a number 1 grade, 80% of the package will be of a number 2 grade and 5% of the package will be of the select structural grade.

Once the package is received it is, at step 204, separated into the three types of lumber in the package—one group for the number 1 grade, a second group for the number two grade and a third group for the select structural grade. In certain embodiments, this separation is performed visually, while in other embodiments, the separation may be performed from some other method such as an optical or acoustic scan of the materials to determine the associated engineering grade. Once the lumber is separated into its engineering grade floor joists can be manufactured from lumber from the various grades in order to meet customer requirements, such as structural integrity or fire resistance.

In addition to the visual or optical inspection for engineering grade, in certain embodiments, at step 206, a mechanical inspection may also be performed. In some embodiments, the mechanical inspection may include an ultrasound measurement to grade a specific engineering value range. In certain embodiments, a Machine Stress-Rated Lumber (MSR) measurement is conducted. The MSR is dimension lumber that has been evaluated by mechanical stress-rating equipment. The stress-rating equipment measures the stiffness of the material and sorts it into various modulus of elasticity (E) classes. One such rating equipment may be an ultrasound lumber rating device. Because you cannot visually grade lumber beyond an engineering value of 1.9e, but lumber as high as 2.1e or 2.3e exists, a non-visual or non-optical method to grade higher grade lumber may be used. An ultrasound lumber rating device is capable of grading lumber higher that 1.9e, if that lumber does indeed satisfy the requirements of having a higher engineering value. Once the mechanical inspection is finished, the lumber will be, at step 208, sorted into additional groups to specify the higher than 1.9e engineering grade lumber. For instance, one or more groups could be created, such as another group for lumber with an engineering grade of approximately 2.1e and yet another group for lumber with an engineering grade of approximately 2.3e.

After the lumber has been separated into the various groups, the floor joist can then be, at step 210, manufactured according to the customer's specifications. Based on the engineering value of the lumber used to make the floor joist, an engineering value or e-value can be assigned to the overall floor joist. By developing products only using the segregated groups of lumber for each component, a product with a specified e-value can be provided to customers.

In certain embodiments, at step 212, inline testing of the floor joist is performed subsequent to finger jointing and gluing the lumber together into the floor joist. In certain embodiments, a stress test that pulls on either end of the floor joist, such as a 60 foot floor joist, under a certain force (lbs/in^2) to ensure the above e-value—a pull test—is performed. In some embodiments, this is the only inline test. Also, in certain embodiments, this test may be performed for each floor joist manufactured but is not always done to failure for each floor joist; rather, samples of the floor joists being manufactured are collected randomly and the pull test is performed again but to failure such that the floor joist comes apart. Statistics are collected in order to achieve a certain WWPA certification. For instance, for a 2×12 floor joist, the minimum standard is 28,000 lbs/in^2 of pulling pressure. In certain embodiments, the inline pull test would be performed from approximately 42000 to 45000 lbs/in^2. In terms of e-value, the 28,000 lbs/in^2 achieves a 1.6e, 32,000 lbs/in^2 achieves 1.8e, 37,500 lbs/in^2 achieves 1.9e, etc., as defined by the WWPA. Accordingly, the floor joists tested at 42000 to 45000 lbs/in^2 would have a higher e-value than 1.9e.

To produce floor joists of various lengths, pieces of lumber are adhered together by cutting finger joints in each piece of lumber and gluing those joints together. The finger joints are produced utilizing knives with a certain profile to produce a finger joint with a certain angle and depth such that a pocket is formed within the joint between the two boards. This will allow the adhesive to stay within the joint as opposed to spraying out to the side. Accordingly, in embodiments of the disclosure, the angle and rake of the finger-joint cutting is utilized to form the pocket.

Turning now to FIG. 1, a cross-sectional view of a finger joint 106 of a floor joist 100, in accordance with an embodiment of this disclosure. FIG. 1 illustrates a floor joist 100 with a thickness T. The floor joist 100 includes a first piece of lumber 102 adhered to a second piece of lumber 104 at a finger joint 106. The first piece of lumber 102 includes fingers 108*a*, and the second piece of lumber 104 includes fingers 108*b*. The fingers 108*a* are cut such that a pocket 110 is created between the fingers 108*a* and a corresponding groove in the second piece of lumber 104, when the first and second pieces of lumber 102 and 104 are adhered together. The fingers 108*b* are cut such that a pocket 110 is created between the fingers 108*b* and a corresponding groove in the first piece of lumber 102, when the first and second pieces of lumber 102 and 104 are adhered together. The pocket 110 may be formed by cutting the pieces of lumber 102, 104 to include fingers 108*a*, 108*b* with grooves between the fingers and a pocket 110 at the bottom of the groove. In one embodiment, the pocket 110 may be formed by having the fingers 108*a* and 108*b* be shorter than a depth of the corresponding groove that receives each finger 108*a* and 108*b*. In another embodiment, the pocket may be formed by utilizing a certain knife angle and rake of the finger-joint cutting tool that cuts the fingers 108*a* and 108*b* into pieces of lumber 102 and 104. In the illustrated embodiment, outermost pockets 110*a* are provided. In other embodiments, there are no outermost pockets 110*a*; rather, in these embodiments, the fingers of the lumber 102 and 104 at the outermost edge of the floor joist 100 would fully extend into the groove with no pocket.

In certain embodiments, the pocket 110 spans an entire width of the floor joist thereby forming a plurality of continuous channels through the entire width of the floor joist. However, in other embodiments, the channel does not span the entire width of the floor joist but rather pockets 110 are intermittently placed throughout the width of the floor joist. Further, in certain embodiments, the corresponding groove may be ground or cut such that it has a rounded shape rather than the triangular shape shown in FIG. 1.

In certain embodiments, an adhesive is utilized to adhere the first piece of lumber 102 to the second piece of lumber 104 at the finger joint 106. The pockets 110 function to provide a space between the fingers 108*a* and 108*b* and the corresponding groove such that when the first and second pieces of lumber 102 and 104 are pressed together at the finger joint 106, the adhesive is not forced out of the groove by the fingers 108*a* or 108*b*. Rather, the adhesive pools within the corresponding groove and pocket 110 and thereby stays within the finger joint 106, as opposed to spraying out of the side of the finger joint 106. This allows for a stronger bond between the first piece of lumber 102 and the second piece of lumber 104 to be formed.

Additionally, in certain embodiments, a heat resistant adhesive may be utilized to adhere the first piece of lumber 102 to the second piece of lumber 104 at the finger joint 106. The heat resistive adhesive will generally contain some percent weight of solids, some percent weight of resorcinol and some percent weight of melamine. Additionally, to provide the heat resistance, an additional heat resistive component may be added. Examples of heat resistive components that may be added are: char formers, such as phosphorus compounds; heat absorbers, such as metal hydrates including aluminum trihydrate (ATH) or magnesium hydroxide; flame quenchers, such as bromine or chlorine based halogen systems; and synergists, such as antimony compounds.

The previously discussed adhesives will provide increased strength and heat resistivity, which, in conjunction with the design aspects previously described, will provide for a floor joist that will meet fire code standards as set by either the IRC or the IBC.

In an exemplary embodiment, the floor joist 100 may be a long floor joist with dimensions of 2×4-2×12 up to 60' in length or a floor joist stud with dimensions of 2×4 & 2×6 in 8', 9', & 10' in length.

Floor joist 100 includes the following benefits: passes International Building Code burn rate standards for floor joist applications; superior straightness when compared to solid wood substitutes; superior stability; less likely to warp or twist than conventional solid lumber, thus a cost saving for end-users with less material going into shorter pieces; easy to cut, nail and drill—behaves just like solid lumber with better stronger dimensional stability; cost effective alternative to other engineered products such as laminated strand lumber & laminated veneer lumber (LSL, LVL), I-Joists and I-Beams; light in weight when compared to green lumber, LSL & LVL making it preferred by builders on the job site (less freight into your location—less freight on outbound deliveries); paper-wrapped so product arrives and stays bright and clean during storage; long-term performance; hourly tension/break tests on joints; and no mold.

Floor joist 100 is typically utilized in the following product applications: long length roof rafters & floor joists; tall walls requiring extreme straightness; headers, columns and posts; residential and commercial and industrial applications.

In certain embodiments, the floor joist 100 is assembled with a waterproof, heat resistant, exterior-type adhesive, meeting the requirements of ASTM product standard D2559 and conforming to WWPA's Glued Products Procedures for Mill Certification and Quality Control, C/QC 101. Limitations on knot size and placement near joints are highly restrictive. Testing and quality-control procedures are rigorous. The exterior-type adhesives for CERT EXT JNTS products are suitable for bonding structural end-jointed and laminated wood products for use in general construction where a high strength, waterproof adhesive bond is required.

In certain embodiments, advantages of using floor joist 100 include: the glue joints are engineered to be stronger than the actual wood fiber; stays straighter than solid-sawn dimensional lumber; less crook; less bow; less twist; surfaced dried; and can be used interchangeably with solid-sawn dimensional lumber of similar grade.

In certain embodiments, the floor joist 100 is a finger-joint lumber product made from Douglas Fir. Upon request, we can produce products with White Fir, Hem/Fir and Spruce/Pine/Fir (SPF).

In certain embodiments, the floor joist 100 includes the following technical specifications: finger-jointed using ⅞" finger length for maximum gluing surface and strong joints, using phenol resorcinol formaldehyde adhesive for exterior quality joints; finger-jointed using Western Wood Products Association Glued Lumber Products Procedures and Standards; interchangeable with solid lumber of the same species and visual grades (American Forest & Paper Association—2005 National Design Specifications s.4.1.6); design Values (bending, tension, compression, stiffness, nail holding) are the same as for solid lumber of the same species and grade; tension tested for roof loading to 21 times design tension value for grade.

The embodiments and examples set forth herein were presented in order to best explain the present disclosure and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of manufacturing a floor joist, the method comprising:
   performing an optical inspection of a package of lumber, wherein the optical inspection determines an engineering grade of individual pieces of lumber within the package of lumber;
   separating the package of lumber into three groups of lumber based on the engineering grade, wherein the three groups of lumber include a first group, a second group and a third group, lumber in the third group of lumber having the highest engineering grade of the three groups of lumber and lumber in the first group of lumber having the lowest engineering grade of the three groups of lumber;

performing a mechanical inspection of the lumber in the third group of lumber to determine a refined engineering value based on the mechanical inspection, wherein the mechanical inspection includes a Machine Stress-Rated Lumber (MSR) measurement to determine a stiffness of the lumber of the third group of lumber;

sorting the lumber of the third group of lumber to include a fourth group of lumber based on the refined engineering value, wherein lumber in the fourth group of lumber has a higher engineering grade than lumber remaining in the third group of lumber; and manufacturing the floor joist using lumber entirely from one of the first group of lumber, second group of lumber, third group of lumber and fourth group of lumber based on a desired engineering value for the floor joist, wherein the lumber in the first group of lumber has a modulus of elasticity of approximately 1.6 e, the lumber in the second group of lumber has a modulus of elasticity of approximately 1.8 e, the lumber in the third group of lumber has a modulus of elasticity of approximately 1.9 e, and the lumber in the fourth group of lumber has a modulus of elasticity greater than 1.9 e.

2. The method of claim 1, wherein the mechanical inspection includes an ultrasound measurement.

3. The method of claim 1, wherein a modulus of elasticity of a floor joist manufactured from the lumber of the first group of lumber is approximately 1.6 e, a modulus of elasticity of a floor joist manufactured from the lumber of the second group of lumber is approximately 1.8 e, a modulus of elasticity of a floor joist manufactured from the lumber of the third group of lumber is approximately 1.9 e, and a modulus of elasticity of a floor joist manufactured from the lumber of the fourth group of lumber is greater than 1.9 e.

4. The method of claim 1, further comprising performing inline testing of the floor joist manufactured using lumber entirely from one of the first group of lumber, the second group of lumber, the third group of lumber, and the fourth group of lumber.

5. The method of claim 4, wherein the inline testing includes a pull test and a Western Wood Products Association (WWPA) certification is assigned to the floor joist based on a result of the pull test.

6. A method of manufacturing a floor joist, the method comprising:

performing an optical inspection of a package of lumber, wherein the optical inspection determines an engineering grade of individual pieces of lumber within the package of lumber;

separating the package of lumber into three groups of lumber based on the engineering grade, wherein the three groups of lumber include a first group, a second group and a third group, lumber in the third group of lumber having the highest engineering grade of the three groups of lumber and lumber in the first group of lumber having the lowest engineering grade of the three groups of lumber;

performing a mechanical inspection of the lumber in the third group of lumber to determine a refined engineering value based on the mechanical inspection, wherein the mechanical inspection includes a Machine Stress-Rated Lumber (MSR) measurement to determine a stiffness of the lumber of the third group of lumber;

sorting the lumber of the third group of lumber to include a fourth group of lumber based on the refined engineering value, wherein lumber in the fourth group of lumber has a higher engineering grade than lumber remaining in the third group of lumber; and manufacturing the floor joist using lumber entirely from the fourth group of lumber, wherein the lumber in the fourth group of lumber has a modulus of elasticity greater than approximately 1.9 e.

* * * * *